US006812215B2

(12) United States Patent
Buchholz et al.

(10) Patent No.: US 6,812,215 B2
(45) Date of Patent: Nov. 2, 2004

(54) COMPOSITIONS FOR THE TREATMENT OF INFLAMMATORY JOINT DISEASES AND OSTEOPOROSIS

(75) Inventors: Herwig Buchholz, Frankfurt (DE); Jerzy Meduski, Playa del Rey, CA (US)

(73) Assignee: Merck Patent Gesellschaft mit beschränkter Haftung, Darmstadt (DE)

( * ) Notice: Subject to any disclaimer, the term of this patent is extended or adjusted under 35 U.S.C. 154(b) by 0 days.

(21) Appl. No.: 10/296,972

(22) PCT Filed: May 19, 2001

(86) PCT No.: PCT/EP01/05753

§ 371 (c)(1),
(2), (4) Date: Dec. 2, 2002

(87) PCT Pub. No.: WO01/91734

PCT Pub. Date: Dec. 6, 2001

(65) Prior Publication Data

US 2003/0139354 A1 Jul. 24, 2003

Related U.S. Application Data

(60) Provisional application No. 60/208,572, filed on Jun. 2, 2000.

(51) Int. Cl.[7] .................... A01N 43/04; A61K 31/70; A61K 31/715

(52) U.S. Cl. ............... 514/27; 514/25; 514/54; 514/886; 514/887; 536/1.11; 536/4.1; 536/8

(58) Field of Search ............. 514/27, 25, 54; 536/1.11, 8, 4.1

(56) References Cited

U.S. PATENT DOCUMENTS 5,478,579 A * 12/1995 Sawruk ............... 424/535
5,807,586 A * 9/1998 Jackson et al. ....... 424/630

FOREIGN PATENT DOCUMENTS

DE    WO 00/25764    * 5/2000

* cited by examiner

Primary Examiner—James O. Wilson
Assistant Examiner—Traviss C. McIntosh, III
(74) Attorney, Agent, or Firm—Millen, White, Zelano & Branigan, P.C.

(57) ABSTRACT

Compositions and pharmaceutical compositions are described which comprise: a component A comprising one or more flavonol glycosides, a component B comprising one or more tetrahydrofolic acid compounds, a component C comprising one or more calcium supplements, and a component D comprising one or more magnesium supplements. Methods of using such compositions and pharmaceutical compositions to treat and/or prevent osteoporosis and/or an inflammatory joint disease are also described.

50 Claims, No Drawings

COMPOSITIONS FOR THE TREATMENT OF INFLAMMATORY JOINT DISEASES AND OSTEOPOROSIS

This invention claims priority of provisional application 60/208,572, filed Jun. 2, 2000.

The present invention relates, e.g., to compositions and pharmaceutical compositions for the treatment and/or prevention of osteoporosis and/or inflammatory joint diseases, methods of treating and/or preventing osteoporosis and/or inflammatory joint diseases and the use of the aforementioned composition for the treatment and/or prevention of osteoporosis and/or inflammatory joint diseases.

BACKGROUND OF THE INVENTION

Osteoporosis (gr: osteon bone; poros hole) is described in general terms as a reduction in bone density with retention of a normal chemical composition. More specifically, osteoporosis is a generalized, progressive diminution of bone density, i.e. bone mass per unit volume, causing skeletal weakness, although the ratio of mineral to organic elements is unchanged. 30 to 40% of the skeletal mass must be lost in order to reliably diagnose osteoporosis by radiology. Contemporary medicine distinguishes between primary and secondary osteoporosis (The Merck Manual of Diagnosis and Therapy, 17th ed., 1999). Primary osteoporosis includes idiopathic osteoporosis, rare but occurring in children and young adults; postmenopausal osteoporosis, occurring between the ages of 50 and 75; and involutional or senile osteoporosis associated with the normal process of aging. It is characterized by a predominant osteoclast activity and a disruption of the feedback mechanism between the serum calcium level and the parathyroid hormone (PTH) secretion. It occurs mainly uniformly throughout the whole skeleton. Secondary osteoporosis, accounting for less than 5% of all osteoporosis cases, includes endocrine dysfunctions. It starts mostly at the main skeleton and progresses centrifugally. Osteoporosis is characterized by pain in the respective bones, diffuse back pain, vertebral body collapse, pathological fractures, in particular, fracture of the neck of the femur. The goal of the management of all types of osteoporosis is therefore to decrease pain, to prevent fractures and to maintain the body functions.

Osteoporosis is a common clinical feature and common complication in patients affected with chronic inflammatory diseases with joint manifestations. These include rheumatoid arthritis (RA), Juvenile Rheumatoid Arthritis (JRA), psoriatic arthritis, Reiter's syndrome (reactive arthritis), Crohn's disease, ulcerative colitis, sarcoidosis (Orcel, P.; Cohen-Solal, M.; de Vernejoul, M. C., and Kuntz, D. [Bone demineralization and cytokines]. Rev Rhum Mal Osteoartic. 1992 September; 59(6 Pt 2):16S–22S; Brown, J. H. and Deluca, S. A. The radiology of rheumatoid arthritis. Am Fam Physician. 1995 Oct; 52(5):1372–80; De Vos, M.; De Keyser, F.; Mielants, H.; Cuvelier, C., and Veys, E. Review article: bone and joint diseases in inflammatory bowel disease. Aliment Pharmacol Ther. 1998 May; 12(5): 397–404; Falcini, F.; Trapani, S.; Civinini, R.; Capone, A.; Ermini, M., and Bartolozzi, G. The primary role of steroids on the osteoporosis in juvenile rheumatoid patients evaluated by dual energy X-ray absorptiometry. J Endocrinol Invest. 1996 March; 19(3):165–9; Scutellari, P. N. and Orzincolo, C. Rheumatoid arthritis: sequences. Eur J Radiol. 1998 May; 27 Suppl 1:S31–8).

Rheumatoid arthritis is associated with a decrease in bone mass (Cortet, B.; Flipo, R. M.; Blanckaert, F.; Duquesnoy, B.; Marchandise, X., and Delcambre, B. Evaluation of bone mineral density in patients with rheumatoid arthritis. Influence of disease activity and glucocorticoid therapy. Rev Rhum Engl Ed. 1997 July–Sep. 30, 1997; 64(7–9):451–8). Typical changes of an inflammatory arthritis include juxta-articular osteoporosis, cartilage loss, and cortical or marginal bone erosions (Lawson, J. P. and Steere, A. C. Lyme arthritis: radiologic findings. Radiology. 1985 January; 154 (1):37–43; Grassi, W.; De Angelis, R.; Lamanna, G., and Cervini, C. The clinical features of rheumatoid arthritis. Eur J Radiol. 1998 May; 27 Suppl 1:S18–24).

Joint inflammation exerts both local and systemic effects on skeletal tissues. Three forms of bone disease (bone loss) have been described in rheumatoid arthritis, namely: focal bone loss affecting the immediate subchondral bone and bone at the joint margins; periarticular osteopenia adjacent to inflamed joints; and generalized osteoporosis involving the axial and appendicular skeleton (Goldring, S. R. and Gravallese, E. M. Mechanisms of bone loss in inflammatory arthritis: diagnosis and therapeutic implications. Arthritis Res. 2000; 2(1):33–7).

During chronic inflammatory joint diseases, such as rheumatoid arthritis, synovial cells produce large amounts of cytokines leading to increased local bone resorption and juxta-articular bone destructions (Orcel, P.; Cohen-Solal, M.; de Vernejoul, M. C., and Kuntz, D. [Bone demineralization and cytokines]. Rev Rhum Mal Osteoartic. 1992 September; 59(6 Pt 2):16S–22S).

The cause of osteoporosis has not been fully clarified. According to one theory, osteoporosis is a calcium dysfunction and the use of calcium supplements has been widely suggested. However, so far, no reossification of the osteoporotic bone after calcium therapy could be demonstrated.

U.S. Pat. No. 5,478,579 describes a method for inducing and enhancing the absorption of calcium into mammalian bone tissue in order to treat metabolic calcium deficiencies in bone tissue, in particular osteoporosis. It was found that ossification of mammalian bone tissue could be enhanced by orally administering to a patient an effective dose of calcium in combination with a flavonol aglycone glycoside. It is believed that the flavonol aglycone glycoside affords an advantageous function through a chelation delivery system. Flavonols possess a benzene ring structure having available bonds to function as a chelate. Therefore, flavonols, due to their particular molecular structure, are capable of holding and delivering certain minerals, including calcium, to mammalian bone tissue. Also bone tissue would naturally absorb flavonol glycosides from the blood stream. It is further disclosed that the combination of the flavonol aglycone glycoside and calcium leads to an increased bone mineral density which would not have been obtainable through the use of simple calcium supplements.

Furthermore, quercetin, which is a related bioflavonoid and differs from the aforementioned flavonol compounds in that it does not contain the glycoside residue, has been shown to inhibit tumor necrosis factor-α induced expression of interleukin 8 (IL-8) and monocyte chemoattractant protein-1 (MCP-1) in cultured human synovial cells. It was therefore suggested that quercetin can be used in the treatment of rheumatoid arthritis which is an autoimmune disorder that involves inflammation mainly in synovial tissues of joints (Sato et al., The Journal of Rheumatology, 1997; 24:9, p. 1680). In addition, the relation between interleukins and cytokines and metabolic bone diseases was studied (Pumarino et al., Rev Med Chile 1996; 124: p. 48). It could be shown that interleukin 1, 6 and 11, transforming growth factor and tumor necrosis factor stimulate osteoclast mediated bone resorption. Interleukin 1 is the most potent bone resorption agent. Although the role of interleukin 1, 6, 11 and the tumor necrosis factors is not quite clear, they appear to have a depressing effect on bone formation.

Cohen et al. (Israel Journal of Medical Sciences, 17, 1981, p. 1123) investigated the cause of an increased crystallinity index in bone tissue found in iliac crest bone samples from postmenopausal osteoporotic women by chemical analysis. The percentage of crystallinity should be regarded as an index that assumes that mature bone is only apatitic and this provides a measure of crystal size and perfection. It could be demonstrated by Cohen et al. that osteoporotic women have low total body magnesium stores. It could also be shown that magnesium exerts its action as a crystal poison in the nucleation and growth of apatite and its precrystalline intermediate. Therefore, osteoporotic bone, i.e. bone mineral with a lower magnesium content, has larger and more perfect crystals and bone mineral with a higher magnesium content has smaller and less perfect crystals than normal bone mineral. It was consequently suggested that the administering of magnesium supplements may be used in osteoporosis therapy.

Homocysteinemia (the accumulation of homocysteine in plasma and tissue) is the result of deficiencies of certain enzymes and/or substrates involved in the transmethylation pathways. It is caused by the accumulation of homocysteine and its two disulfides in plasma and tissue (Mudd et al., The Metabolic Basis of Inherited Disease, New York, McGraw-Hill, 1978, p. 458). Homocysteinemia is associated with juvenile arteriosclerosis, recurrent arterial and venous thromboembolic manifestations and osteoporosis. The latter may be due to the fact that homocysteine also interferes with collagen synthesis, and it is this interaction that may be significant in the development of defective bone matrix and osteoporosis (Am J Med Sci, 273, 1977, p. 120). Folic acid has been described as a successful tool for the treatment of hyperhomocysteinemia (Brattström et al., Metabolism, Vol. 34, No. 11, 1985, p. 1073). The metabolite transforming homocysteine to methionine is the active form of folic acid: 5-methyl-tetrahydrafolic acid (5-MTHF). Depending on the degree of methylene tetrahydrofolate reductase (MTHFR) dysfunction, the body can less or more easily transform the various forms of folates into 5-MTHF.

The effectiveness of the previously proposed compounds or compositions is, however, generally not satisfactory and there remains a need of providing a more effective treatment of osteoporosis and/or inflammatory joint diseases.

SUMMARY OF THE INVENTION

It is an object of the present invention to provide a new composition with improved effects for the treatment and/or the prevention of osteoporosis and/or inflammatory joint diseases.

Upon further study of the specification and appended claims, further objects and advantages of this invention will become apparent to those skilled in the art.

One object has been achieved by a composition comprising the following components in combination:
  a component A comprising one or more flavonol glycosides,
  a component B comprising one or more tetrahydrofolic acid compounds,
  a component C comprising one or more calcium supplements, and
  a component D comprising one or more magnesium supplements.

The present invention provides also a pharmaceutical composition comprising the following components in combination:
  a component A comprising one or more flavonol glycosides,
  a component B comprising one or more tetrahydrofolic acid compounds,
  a component C comprising one or more calcium supplements,
  a component D comprising one or more magnesium supplements, and
  a pharmaceutically suitable carrier, diluent, vehicle and/or exipient.

Moreover, the present invention is directed to a method of treating and/or preventing osteoporosis and/or an inflammatory joint disease, comprising administering to a mammal in need thereof a therapeutically effective amount of a composition comprising the following components in combination:
  a component A comprising one or more flavonol glycosides,
  a component B comprising one or more tetrahydrofolic acid compounds,
  a component C comprising one or more calcium supplements, and
  a component D comprising one or more magnesium supplements.

Finally, the present invention is directed to the use of a composition comprising the following components in combination:
  a component A comprising one or more flavonol glycosides,
  a component B comprising one or more tetrahydrofolate acid compounds,
  a component C comprising one or more calcium supplements, and
  a component D comprising one or more magnesium supplements for the treatment and/or prevention of osteoporosis and/or inflammatory joint diseases.

Firstly, the composition in accordance with the present invention will be described in more detail.

According to the present invention, the composition comprises a component A comprising one or more of flavonol glycosides. The flavonol glycosides contain a flavone skeleton of the following general structure of formula (1):

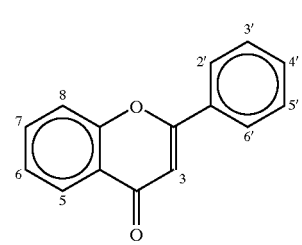

This skeleton forms the sugar-free part of the flavonoids and is also generally referred to as an aglycone. Any aglycone can be used. Preferably, the aglycone is represented by formula (2) shown below:

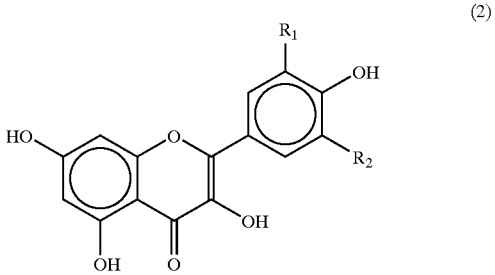

(2)

wherein $R_1$ and $R_2$ are independently hydrogen, hydroxy or a methoxy group. Preferable examples of the aglycones are quercetin ($R_1$=OH, $R_2$=H), kaempferol ($R_1$=H, $R_2$=H), myricetin ($R_1$=OH, $R_2$=OH) and isorhamnetin ($R_1$=OCH$_3$, $R_2$=H). These aglycones are preferred since they occur in nature and are, thus, readily available. Particularly preferred is the aglycone quercetin.

The flavonol glycoside contains a sugar residue which is bound via a glycosidic bond to the aglycone leading to structures of the formulae (3), (4) or (5) shown below.

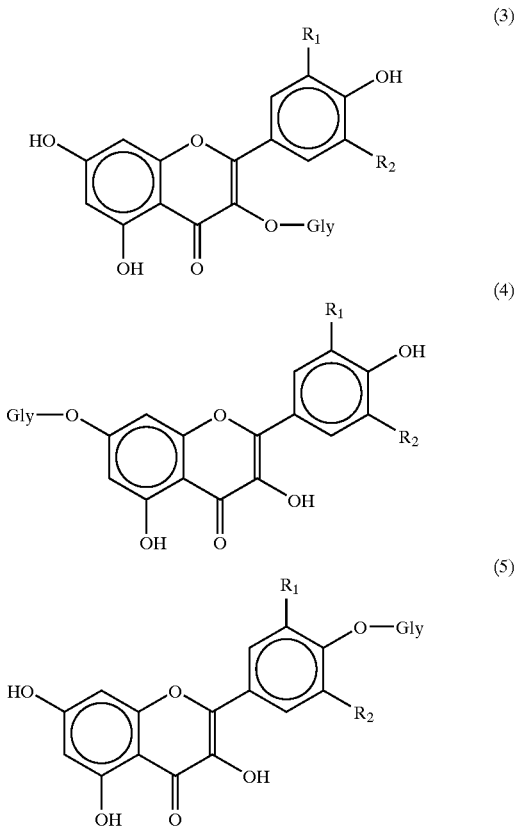

wherein $R_1$ and $R_2$ have the same meaning as described above and Gly is a mono- or oligoglycoside residue. Preferably, Gly represents a mono-, di- or triglycoside. The glycoside is preferably selected from hexosyl residues, specifically rhamnesyl, glucosyl, galactosyl and mannosyl residues.

Specific examples of the flavonol glycoside used in the present invention include glycosides of quercetin such as quercetin-3-O-galactoside (hyperoside), quercetin-3-O-glucoside (isoquercetin), quercetin-3-O-rhamnoside (quercitrin), quercetin-3-O-rutinoside (rutin), quercetin-7-O-glucoside (quercimeritrin), quercetin-4'-O-glucoside (spiraeosid) and quercetin-3-O-galactoside (hyperin). As an example of a flavonol glycoside of the aglycone kaempferol, kaempferol-3-O-glucoside (astragalin) may be mentioned. Myricetin-3-O-digalactoside is an example of a flavonol glycoside of the aglycone myricetin. An example of a flavonol glycoside of the aglycone isorhamnetin is isorhamnetin-3-O-rutinoside (narcissin). The flavonol glycosides isoquercetin, quercetrin, isoquercetrin, quercimeritrin, spiraeosid, rutin and hyperin are particularly preferred.

The flavonol glycosides may be obtained from any source, e.g., plants, in particular herbs. Herbs known to contain for example quercetin glycosides are described in U.S. Pat. No. 5,478,579.

The composition according to the present invention comprises component A in an effective amount in order to exert the desired effect in the treatment and/or prevention of osteoporosis and/or inflammatory joint diseases.

The composition according to the present invention comprises component A in an effective amount in order to exert the desired effect in the treatment and/or prevention of osteoporosis and/or inflammatory joint diseases. Typically, an amount of about 0.1–25.0 weight % of the total, preferably about 0.2–12.5 weight %, and most preferably about 0.5–10.0 weight % is used.

The dosage of component A is preferably selected to comprise 25 to 1000 mg, preferably 40 to 500 mg per daily dose.

The composition in accordance with the present invention comprises further a component B comprising one or more tetrahydrofolic acid compounds.

The tetrahydrofolic acid compound is a derivative of folic acid. Folic acid is metabolized in the body via dihydrofolic acid under the action of the enzyme dihydrofolate reductase into tetrahydrofolic acid. Examples of the tetrafolic acid compound used in the present invention include tetrahydrofolic acid and derivatives thereof as well as physiologically acceptable salts thereof. The derivatives are preferably selected from methyl derivatives or compounds which may be converted enzymatically into the methyl derivative. It is particularly preferred to use 5-methyltetrahydrofolic acid and physiological acceptable salts thereof as well as compounds which may be converted in the body into the 5-methyl derivative. Thus, the tetrahydrofolic acid compound is preferably selected from tetrahydrofolic acid, 5-methyltetrahydrofolic acid, 5-formyltetrahydrofolic acid, 10-formyltetrahydrofolic acid, 5,10-methylenetetrahydrofolic acid, 5,10-methenyltetrahydrofolic acid or physiologically acceptable salts thereof. The tetrahydrofolic acid compound may be used alone or as a mixture. It particularly preferred to use 5-formyltetrahydrofolic acid or physiologically acceptable salts thereof. Examples of physiologically acceptable salts are alkaline metal or alkaline earth metal salts, such as sodium or calcium salts.

Component B is present in the composition in accordance with the invention in an amount effective for the treatment and/or prevention of osteoporosis and/or inflammatory joint diseases. Typically, component B is present in an amount of about 0.002–0.15 weight % of the total, preferably about 0.004-0.07 weight % and most preferably about 0.01–0.02 weight %.

The composition in accordance with the present invention comprises component B preferably in an amount of 400 to 5000 µg, more preferably 500 to 4000 µg per daily dose.

The composition in accordance with the present invention contains further a component C comprising one or more calcium supplements. The calcium supplement is preferably selected from elemental calcium and calcium compounds. The calcium compound can be selected from calcium oxide and calcium salts of organic or inorganic acids. Preferred examples of the calcium salts include calcium salts of inorganic acids, e.g. calcium carbonate, calcium salts of organic acids such as calcium citrate, calcium lactate, calcium gluconate and, in particular, calcium salts of amino acids such as calcium glycinate and calcium lysinate.

Component C is present in the composition in accordance with the invention in an amount effective for the treatment and/or prevention of osteoporosis and/or inflammatory joint diseases. Typically, component C is used in an amount of about 2.0–50.0 weight % of the total, preferably about 5.0–25.0 weight % and most preferably about 10.0–20.0 weight %.

The composition in accordance with the present invention comprises component C preferably in an amount of 400 to 2000 mg, more preferably 500 to 800 mg per daily dose.

The composition of the present invention also comprises a component D comprising one or more magnesium supplements. The magnesium supplement is preferably selected from elemental magnesium and magnesium compounds. As magnesium compounds, magnesium oxide and magnesium salts of organic or inorganic acids are typically employed. Preferred examples of magnesium salts include magnesium salts of inorganic acids, such as magnesium glycerophosphate and magnesium chloride, magnesium salts of organic acids such as magnesium citrate, magnesium lactate and magnesium gluconate and, in particular, magnesium salts of amino acids such as magnesium glycinate and magnesium taurinate.

Component D is present in the composition of the invention in an effective amount for the treatment and/or prevention of osteoporosis and/or inflammatory joint diseases. Component D is therefore typically used in an amount of about 0.5–30.0 weight % of the total, preferably about 1.2–25.0 weight % and most preferably about 2.5–17.5 weight % in the composition of the present invention.

The composition of the present invention contains component D preferably in an amount of 100 to 1200 mg, more preferably 300 to 1000 mg per daily dose.

A pharmaceutical composition of the present application comprises the aforementioned components and additionally a pharmaceutically suitable carrier, diluent, vehicle and/or exipient. The pharmaceutical composition is present in a suitable pharmaceutical form including solid, semi-solid, liquid or lyophilized formulations such as tablets, powders, capsules, suppositories, suspensions and aerosols. Preferably, the pharmaceutical form is a tablet or a capsule for oral administration. The suitable vehicles, carriers, diluents and/or excipients may be selected depending on the intended use.

Acceptable methods for preparing suitable pharmaceutical forms of the pharmaceutical composition of the present invention are known to those skilled in the art. For example, pharmaceutical preparations may be prepared following conventional techniques of the pharmaceutical chemist involving steps such as mixing, granulating and compressing the necessary tablet forms, or mixing, filling and dissolving the ingredients as appropriate, to give the desired products for oral, parenteral, topical, transdermal, intravaginal, intranasal, intrabronchial, intraocular, intraaural and/or rectal administration. Illustrative examples of such methods includes those described in Remington's Pharmaceutical Sciences, 18th edition (1990).

Solid or liquid pharmaceutically acceptable carriers, diluents, vehicles or excipients may be employed in the pharmaceutical compositions of the present invention. Illustrative solid carriers include starch, lactose, calcium sulfate dihydrate, terra alba, sucrose, talc, gelatine, agar, pectin, acacia, magnesium stearate and stearic acid. Illustrative liquid carriers include syrup, peanut oil, olive oil, saline solution and water. The carrier or diluent may include a suitable prolonged release material such as glycerol monostearate or glycerol distearate, alone or with other auxiliaries. When a liquid carrier is used, the preparation may be in the form of a syrup, elixier, emulsion, soft gelatin capsule, sterile injectable liquid (e.g. solution) or a non-aqueous or aqueous liquid suspension.

The aforementioned composition or pharmaceutical composition of the present invention is employed in the treatment and/or prevention of osteoporosis and/or inflammatory joint diseases. Administration of the composition of the pharmaceutical composition of the present invention may be performed according to any of the accepted modes of adminstration available to those skilled in the art. Illustrative examples of suitable modes of administration include oral, nasal, parenteral, topical, transdermal, intravaginal, intranasal, intrabronchial, intraocular, intraaural and rectal. Preferably, the mode of adminstration is oral.

The specific dose for each patient depends on a wide variety of factors, for example on the activity of the specific compounds employed, the age, body weight, general state of health, sex, diet, the time and route of adminstration, the rate of excretion, the medicinal substance combination and severity of the particular disorder for which the therapy is applied.

Among the conditions or diseases which can be treated and/or prevented by the composition or pharmaceutical composition of the invention are, e.g., any form of osteoporosis (e.g., primary osteoporosis, including, e.g., idiopathic osteoporosis, postmenopausal osteoporosis, and involutional or senile osteoporosis, or secondary osteoporosis, including, e.g., endocrine dysfunctions) and inflammatory joint disease (e.g., rheumatoid arthritis, juvenile arthritis, infectious arthritis, ankylosing spondilitis, osteoarthritis, anrthralgias and other chronic inflammatory diseases associated with joint manifestations).

Advantages of the invention include, e.g., improved joint function (improved joint movement, decrease of morning stiffness, etc.) and reduced signs of inflammation (e.g., pain or swelling).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any whatsoever.

In the foregoing and in the following examples, all temperatures are set forth uncorrected in degrees Celsius; and, unless otherwise indicated, all parts and percentages are be weight.

The entire disclosure of all applications, patents and publications, cited above is hereby incorporated by reference.

EXAMPLES

Example 1

An oral formulation according to the invention is obtained by mixing:

Quercetin-3-O-glucoside (isoquercetin)—500 mg
5-methyltetrahydrofolic acid calcium salt—800 μg
Calcium citrate tetrahydrate—4000 mg (844 mg Ca)

Magnesium chloride hexahydrate—3000 mg (360 mg Mg)

Example 2

An oral formulation according to the present invention is obtained by mixing:

Quercetin-3-O-glucoside (isoquercetin)—200 mg
5-methyltetrahydrofolic acid calcium salt—400 µg
Calcium lysinate (Ca, 12%)—1600 mg
Calcium glycinate (Ca, 20%)—200 mg
Magnesium citrate, dibasic (Mg, 11%)—1000 mg The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A composition comprising:
    a component A comprising one or more flavonol glycosides,
    a component B comprising one or more tetrahydrofolic acid compounds,
    a component C comprising one or more calcium supplements selected from calcium carbonate,
    a calcium citrate, calcium lactate, calcium gluconate, or a calcium salt of an amino acid and
    a component D comprising one or more magnesium supplements selected from magnesium oxide, magnesium glycerophosphate, nagnesium chloride, magnesium citrate, magnesium lactate, magnesium gluconate or a magnesium salt of an amino acid.

2. The composition according to claim 1, wherein component A comprises one or more of a flavonol mono-, di- or triglycoside containing the aglycone, quercetin.

3. The composition according to claim 1, wherein component A is isoquercetin, quercitrin, isoquercitrin, quercimeritrin, spiraeosid, rutin or hyperin.

4. The composition according to claim 1, wherein component A is 0.1–25.0 weight % of the total composition.

5. The composition according to claim 1, wherein component B comprises one or more of tetrahydrofolic acid, 5-methyltetrahydrofolic acid, 5-formyltetrahydrofolic acid, 10-formyltetrahydrofolic acid, or 5,10-methylenetetrahydrofolic acid, or 5,10-methenyltetrahydrofolic acid, or a physiologically acceptable salt thereof.

6. The composition according to claim 1, wherein component B comprises 5-formyl-tetrahydrofolic acid or a physiologically acceptable salt thereof.

7. The composition according to claim 1, wherein component B is 0.002–0.15 weight % of the total composition.

8. The composition according to claim 1, wherein component C is calcium citrate tetrahydrate.

9. The composition according to claim 1, wherein component C is 2.0–50.0 weight % of the total composition.

10. The composition according to claim 1, wherein said component D is magnesium gluconate.

11. The composition according to claim 1, wherein component D is 0.5–30.0 weight % of the total composition.

12. A method for the treatment of osteoporosis, rheumatoid arthritis, juvenile rheumatoid arthritis, psoriatic arthritis, infectious arthritis, ankylosing spondilitis, osteoarthritis, anrthralgias, Reitzer's syndrome, Crohn's disease, ulcerative colitis and/or sarcoidosis comprising administering to a patient in need thereof an effective amount of a composition according to claim 1.

13. A pharmaceutical composition comprising:
    a component A comprising one or more flavonol glycosides,
    a component B comprising one or more tetrahydrofolic acid compounds,
    a component C comprising one or more calcium supplements selected from calcium carbonate, calcium citrate, calcium lactate, calcium gluconate, or a calcium salt of an amino acid and
    a component D comprising one or more magnesium supplements selected from magnesium oxide, magnesium glycerophosphate, magnesium chloride, magnesium citrate, magnesium lactate, magnesium gluconate or a magnesium salt of an amino acid.

14. The pharmaceutical composition according to claim 13, wherein component A comprises one or more of a flavonol mono-, di- or triglycoside containing the aglycone, quercetin.

15. The pharmaceutically composition according to claim 13, wherein component A is isoquercetin, quercitrin, isoquercitrin, quercimeritrin, spiraeosid, rutin or hyperin.

16. The pharmaceutical composition according to claim 13, wherein component A is 0.1–25.0 weight % of the total composition.

17. The pharmaceutical composition according to claim 13, wherein component B comprises one or more of tetrahydrofolic acid, 5-methyltetrahydrofolic acid, 5-formyltetrahydrofolic acid, or 10-formyltetrahydrofolic acid, 5,10-methylenetetrahydrofolic acid, or 5,10-methenyltetrahydrofolic acid, or a physiologically acceptable salt thereof.

18. The pharmaceutical composition according to claim 13, wherein component B comprises 5-formyl-tetrahydrofolic acid or a physiologically acceptable salt thereof.

19. The pharmaceutical composition according to claim 13, wherein component B is 0.002–0.15 weight % of the total composition.

20. The pharmaceutical composition according to claim 13, wherein component C is calcium citrate.

21. The pharmaceutical composition according to claim 13, wherein component C is 2.0–50.0 weight % of the total composition.

22. The composition according to claim 13, wherein said component D is magnesium gluconate.

23. The pharmaceutical composition according to claim 13, wherein component D is 0.5–30.0 weight % of the total composition.

24. A method for the treatment of osteoporosis rheumatoid arthritis, juvenile rheumatoid arthritis, psoriatic arthritis, infectious arthritis, ankylosing spondilitis, osteoarthritis, anrthralgias, Reitzer's syndrome, Crohn's disease, ulcerative colitis and/or sarcoidosis comprising administering to a patient in need thereof an effective amount of a composition according to claim 13.

25. A method of treating osteoporosis comprising administering to a mammal in need thereof a therapeutically effective amount of a composition comprising:
    a component A comprising one or more flavonol glycosides,
    a component B comprising one or more tetrahydrofolic acid compounds, a component C comprising one or more calcium supplements selected from calcium carbonate, calcium citrate, calcium lactate, calcium gluconate, or a calcium salt of an amino acid and a component D comprising one or more magnesium supplements selected from magnesium oxide, magnesium glycerophosphate, magnesium chloride, magnesium citrate, magnesium lactate, magnesium gluconate or a magnesium salt of an amino acid.

26. The method according to claim 25, wherein component A comprises one or more of a flavonol mono-, di- or triglycoside containing the aglycone, quercetin.

27. The method according to claim 25, wherein component A comprises one or more of isoquercetin, quercitrin, isoquercitrin, quercimeritrin, spiraeosid, rutin or hyperin.

28. The method according to claim 25, wherein component A is 0.1–25.0 weight % of the total composition.

29. The method according to claim 25, wherein component B comprises one or more of tetrahydrofolic acid, 5-methyltetrahydrofolic acid, 5-formyltetrahydrofolic acid, 10-formyltetrahydrofolic acid, 5,10-methylenetetrahydrofolic acid, or 5,10-methenyltetrahydrofolic acid, or a physiologically acceptable salt thereof.

30. The method according to claim 25, wherein component B comprises 5-formyltetrahydrofolic acid or a physiologically salt thereof.

31. The method according to claim 25, wherein component B is 0.002–0.15 weight % of the total composition.

32. The method according to claim 25, wherein component C is calcium citrate.

33. The method according to claim 25, wherein component C is 2.0–50.0 weight % of the total composition.

34. The method according to claim 25, wherein said component D is magnesium gluconate.

35. The method according to claim 25, wherein component D is 0.5–30.0 weight % of the total composition.

36. The method according to claim 25, wherein the mammal is a human.

37. A method of treating an inflammatory disease comprising administering to a mammal in need thereof a therapeutic effective amount of a composition comprising:

a component A comprising one or more flavonol glycosides, a component B comprising one or more tetrahydrofolate acid compounds, a component C comprising one or more calcium supplements selected from calcium carbonate, calcium citrate, calcium lactate, calcium gluconate, or a calcium salt of an amino acid and p1 a component D comprising one or more magnesium supplements selected from magnesium oxide, magnesium glycerophosphate, magnesium chloride, magnesium citrate, magnesium lactate, magnesium gluconate or a magnesium salt of an amino acid.

38. The method according to claim 37, wherein component A comprises one or more of a flavonol mono-, di- or triglycoside containing the aglycone, quercetin.

39. The method according to claim 37, wherein component A comprises one or more of isoquercetin, quercitrin, isoquercitrin, quercimeritrin, spiraeosid, rutin or hyperin.

40. The method according to claim 37, wherein component A is 0.1–25.0 weight % of the total composition.

41. The method according to claim 37, wherein component B comprises one or more of tetrahydrofolic acid, 5-methyltetrahydrofolic acid, 5-formyltetrahydrofolic acid, 10-formyltetrahydrofolic acid, 5,10-methylenetetrahydrofolic acid, or 5,10-methenyltetrahydrofolic acid, or a physiologically acceptable salt thereof.

42. The method according to claim 37, wherein component B comprises 5-formyltetrahydrofolic acid or a physiologically acceptable salt thereof.

43. The method according to claim 37, wherein component B is 0.002–0.15 weight % of the total composition.

44. The method according to claim 37, wherein component C is calcium citrate.

45. The method according to claim 43, wherein component C is 2.0–50.0 weight % of the total composition.

46. The method according to claim 37, wherein component D is magnesium gluconate.

47. The method according to claim 37, wherein component D is 0.5–30.0 weight % of the total composition.

48. The method according to claim 37, wherein the mammal is human.

49. The method according to claim 37, wherein said inflammatory disease is rheumatoid arthritis, juvenile rheumatoid arthritis, psoriatic arthritis, infectious arthritis, ankylosing spondilitis, osteoarthritis, anrthralgias, Reitzer's syndrome, Crohn's disease, ulcerative colitis and/or sarcoidosis.

50. A method according to claim 24, wherein said method is for treating rheumatoid arthritis, juvenile rheumatoid arthritis, psoriatic arthritis, infectious arthritis, ankylosing spondilitis, osteoarthritis, anrthralgias, Reitzer's syndrome, Crohn's disease, ulcerative colitis and/or sarcoidosis.

* * * * *

UNITED STATES PATENT AND TRADEMARK OFFICE
CERTIFICATE OF CORRECTION

PATENT NO. : 6,812,215 B2
DATED : November 2, 2004
INVENTOR(S) : Herwig Buchholz It is certified that error appears in the above-identified patent and that said Letters Patent is hereby corrected as shown below:

Column 9,
Line 35, reads "nagnesium", should read -- magnesium --.

Column 12,
Line 1, delete "p1".

Signed and Sealed this

Second Day of August, 2005

JON W. DUDAS
*Director of the United States Patent and Trademark Office*